United States Patent [19]

Amir et al.

[11] Patent Number: 5,701,909
[45] Date of Patent: Dec. 30, 1997

[54] MACHINE AND METHOD FOR THE DETERMINATION OF NERVOUS-SYSTEM-GENERATOR PARAMETERS USING LEAD FIELDS

[75] Inventors: Avner Amir, Ramat-Yishay, Israel; Daniel John Fletcher, San Francisco; Don Lee Jewett, Mill Valley, both of Calif.

[73] Assignee: Abratech Corporation, Sausalito, Calif.

[21] Appl. No.: 679,704

[22] Filed: Jul. 11, 1996

Related U.S. Application Data

[63] Continuation-in-part of Ser. No. 333,475, Nov. 1, 1994, abandoned.

[51] Int. Cl.$^6$ ............................................. A61B 5/0476
[52] U.S. Cl. ........................................ 128/731; 128/733
[58] Field of Search .................................. 128/731–734, 128/741; 607/118

[56] References Cited

U.S. PATENT DOCUMENTS 5,568,816  10/1996  Gevins et al. ..................... 128/731

OTHER PUBLICATIONS

Schneider, Michel R. "A Multistage Process for Computing Virtual Dipolar Sources of EEG Discharges from Surface Information," *IEEE Transactions on Biomedical Engineering* BME–19(1): 1–12 (1972).

Scherg, Michael. "Fundamentals of Dipole Source Potential Analysis," in *Auditory Evoked Magnetic Fields and Potential*, Eds: Hoke, M.; Grandori, F.; Romani, G.L. *Adv. Audiol.* 6: XX–XX, (Basel, Karger 1989).

Cuffin, B. Neil et al. "Tests of EEG Localization Accuracy Using Implanted Sources in the Human Brain," *Annals of Neurology* 29: 132–138 (1991).

Mosher, John C.; Lewis, Paul S.; Leahy, Richard M. "Multiple Dipole Modeling and Localization from Spatio–Temporal MEG Data," *IEEE Transactions on Biomedical Engineering* 39(6): 541–557 (1992).

Balish, M. et al. "Localization of implanted dipoles by magnetoencephalography," *Neurology* 41: 1072–1076 (1991).

Roth, Bradley J. et al. "How well does a three–sphere model predict positions of dipoles in a realistically shaped head?" *Electroencephalography and clinical Neurophysiology* 87: 175–184 (1993).

Oostendorp, Thom F.; Van Oosterom, Adriaan. "Source Parameter Estimation in Inhomogeneous Volume Conductors of Arbitrary Shape," *IEEE Transactions on Biomedical Engineering* 36(3): 382–391 (1989).

He, Bin et al. "Electric Dipole Tracing in the Brain by Means of the Boundary Element Method and Its Accuracy," *IEEE Transactions on Biomedical Engineering* BME–34(6): 406–414 (1987).

*Primary Examiner*—Jeffrey R. Jastrzab
*Attorney, Agent, or Firm*—Virginia H. Meyer

[57] ABSTRACT

The invention is an improved machine and method for converting recordings of electric potentials into nervous-system-generator parameters that can be used by clinicians and researchers to evaluate generators of central or peripheral nervous system activity. The machine and method utilize as inputs physiological recordings made at sites remote from the generator, data on shapes of boundaries, locations of recording points and electrical conductivity of volumes to be analyzed. The invention teaches how to compute the weight function values, corresponding to electric potentials and/or electric fields across a pair of electrodes due to unit source current by the use of the Lead Field Analysis in a boundary element method.

8 Claims, 5 Drawing Sheets

MACHINE AND METHOD FOR THE DETERMINATION OF NERVOUS-SYSTEM-GENERATOR PARAMETERS USING LEAD FIELDS

RELATED APPLICATION

This application is a continuation-in-part of pending U.S. Ser. No. 08/333,475 filed Nov. 1, 1994, now abandoned.

GOVERNMENT RIGHTS

This invention was made with United States government support under grant numbers R01 DC00328 and R43NS32219 awarded by the National Institutes of Health. The United States government has certain rights in the invention.

TECHNICAL FIELD

This invention is related to a machine and improved method for converting recordings of electric potentials into displayed electrical generator parameters. The machine and method can be used by clinicians and researchers to evaluate generators of central or peripheral nervous system activity. The machine and method are based on a new analysis system that utilizes lead fields as one part of the necessary computations.

BACKGROUND

In both clinical practice and research, it is often necessary to determine whether the activity in a given area of the central or peripheral nervous system has changed, either due to disease or due to some experimental manipulation. Where it is not possible to directly measure changes at the relevant nervous system area, indirect measurements are made by non-invasively recording the nervous system activity from remote sites. For the brain, the remote sites are at the surface of the scalp or brain; for other parts of the nervous system, they are at the surface of the body. In either case, the activity may be measured as electric potentials, which emanate from so-called "nervous-system-generators" in the brain or other parts of the nervous system.

Figure 1:
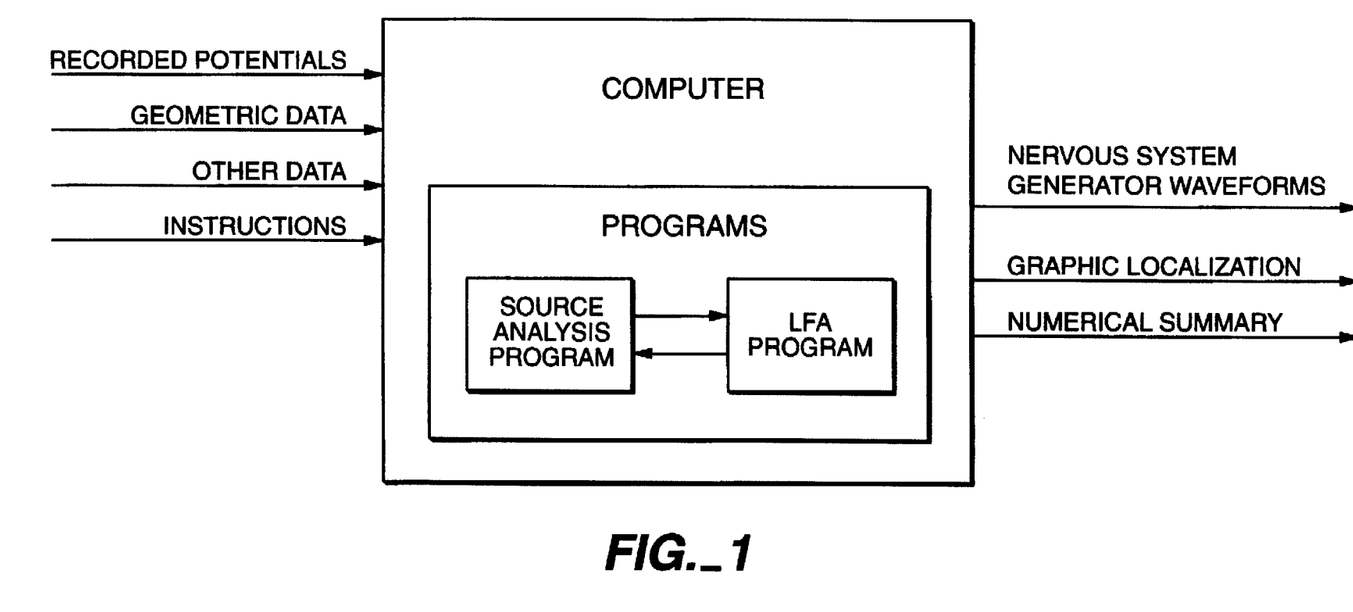
FIG. 1 is a diagram showing a machine that converts recorded electric potentials, geometric data, and other inputs, into nervous-system-generator parameters, such as waveforms, locations, and other information.

The parameters of the nervous-system-generators corresponding to the recorded potentials are then derived, using the recorded data and general purpose computers specifically programmed to estimate and display the most probable parameters of the generators in question. These parameters include, but are not necessarily limited to, location, orientation, and magnitude. Such parameters are used by clinicians and researchers in evaluating whether the activity in a given area of the nervous system has changed. A diagram of a device that carries out the transformation of recorded potentials into nervous-system-generator parameters such as nervous-system-generator waveforms and graphic display of localization and orientation is shown in FIG. 1.

For the brain, this type of determination of nervous-system-generator parameters is referred to herein as "Brain-Generator Source Characterization" (B-GSC). B-GSC is presently done by either a so-called Dipole Source Location method (DSL [Schneider M., *IEEE Trans. Biomed. Eng.* BME-19: 1–12, 1972; Scherg M., *Adv. Audiol.* 6:40–69, 1990]) or by a MUltiple SIgnal Classification method (MUSIC [Mosher J. C., Lewis P. S., Leahy R. M., *IEEE Trans. Biomed. Engin.*, BME-39:541–557, 1992]). With both DSL and MUSIC the transformations of the remotely-recorded potentials or fields into brain generator parameters are commonly done by computing in such a way that the shape of the head is treated as a sphere. The human head is not a sphere, and it has now been shown that computing as if the head were a sphere can lead to significant errors [Cuffin, et. al. *Annals of Neurology*, 29:132–138, 1991; Balish, et. al. *Neurology*, 41:1072–1076, 1991; Roth, Balish, Gorbach, Sato, *Electroenceph. clin. Neurophysiol.*, 87:175–184, 1993]. To correct this problem, some in the art have tried to compute in more realistic head shapes using the Boundary Element Method (BEM) [Oostendorp, van Oosterom, *IEEE Trans Biomed Eng*, 36:382–391, 1989; He, et. al. *IEEE Trans Biomed Eng*, 34:406–414, 1987] or the Finite Element Method (FEM) [Y. Yan, P. L. Nunez, R. T. Hart: Finite element model of the human head: scalp potentials due to dipole sources. *Medical and Biological Engineering and Computing*, 29:475–481, 1991]. Aspects of the computation must be optimized for different brain-generator locations, which is an inefficient and sometimes lengthy procedure, requiring a very high performance computer.

Thus there is a need for a machine that can contain a smaller computer, using a method that can calculate brain generator parameters when the shape of the head is not presumed to be a sphere, and that does not need to be optimized for each brain-generator location. Our invention provides such a machine and method, and is based on a system we call Lead Field Analysis (LFA).

Figure 2:
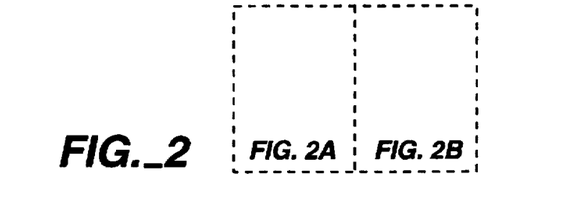
FIG. 2 (A and B) is a diagram showing the sequence of steps that are used in converting electric potentials to nervous-system-generator parameters by a presently-available method that utilizes a spherical shape to derive weight function values (FIG. 2A), together with the standard method of computing weight function values from a boundary-element method (FIG. 2B, left side, boxes A1 and A2), together with the improved method of the invention (FIG. 2B, right side, boxes B1 and B2).
Figure 2A:
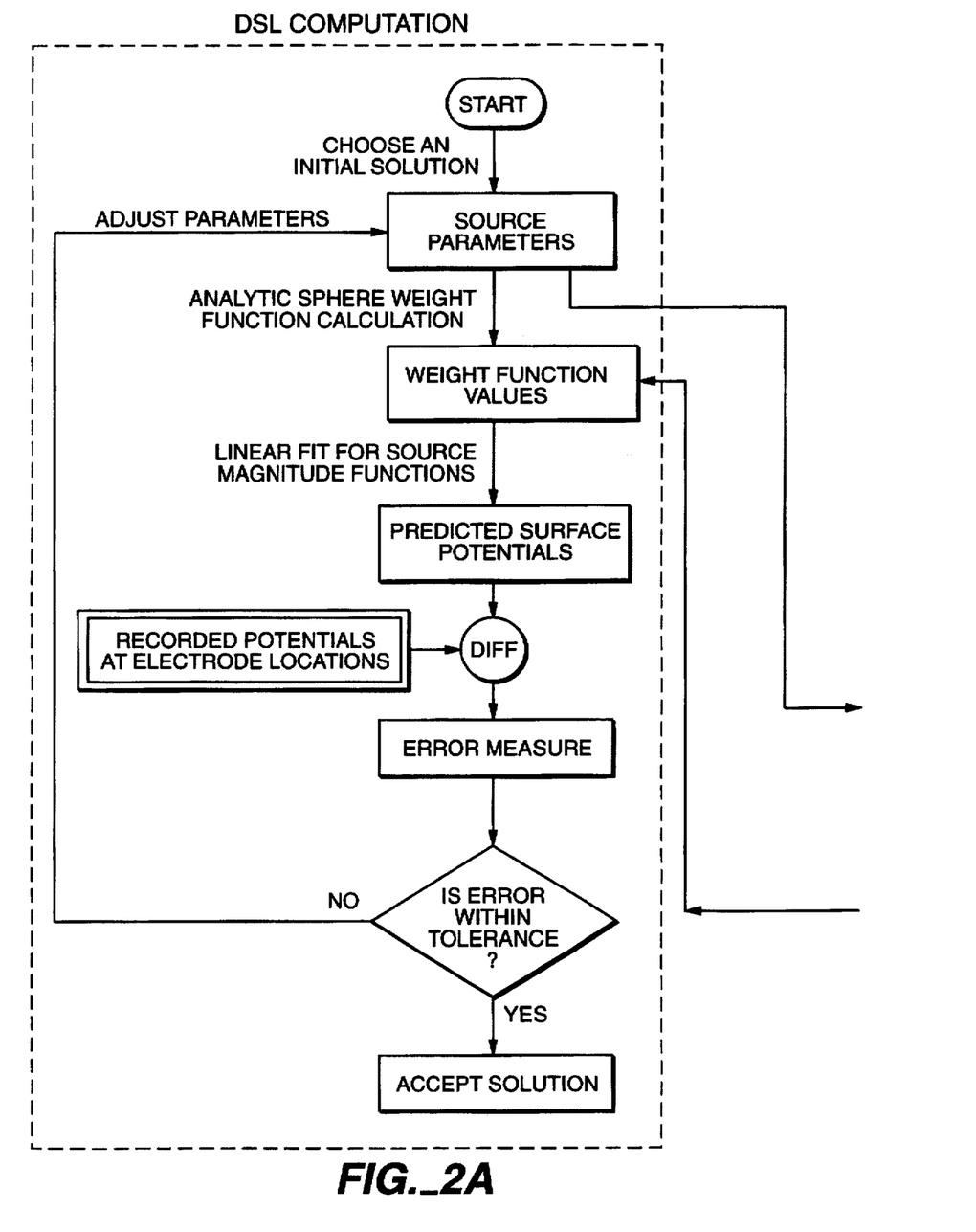
Figure 2B:
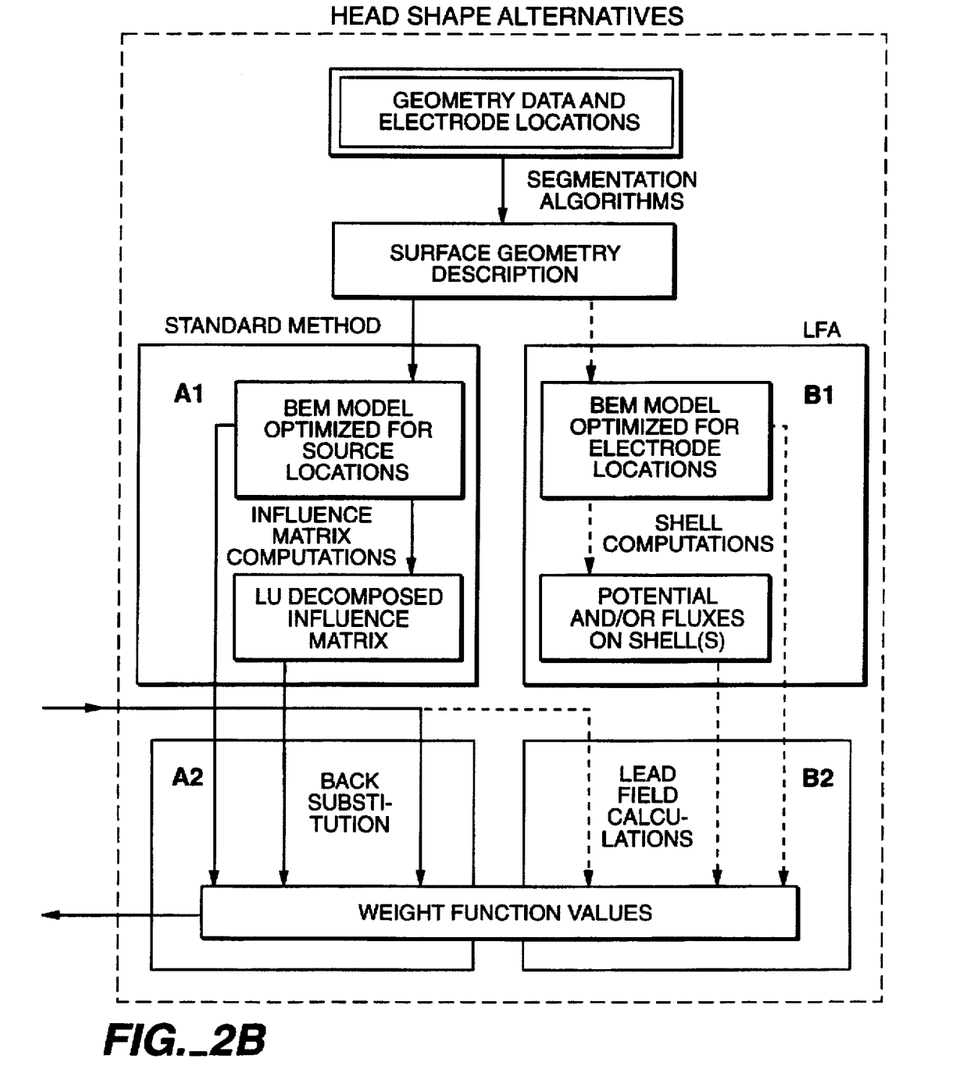

FIG. 2 shows a stepwise outline of some different methods for determining brain-generator activity using a Dipole Source Localization (DSL) method, computing either (1) in a sphere, (2) in a head shape using the standard Boundary Element Method (BEM) or Finite Element Method (FEM), or (3) in a head shape using the Lead Field Analysis system of our invention. As FIG. 2 illustrates, the steps in the commonly-used DSL include transformation of chosen dipole source parameters into weight function values using analytic calculations based upon a sphere (see second downward arrow from the top in the box at the left of FIG. 2A). In order to determine dipole source parameters in a head shape, rather than a sphere, one can use a BEM or FEM. These methods substitute in the DSL for the "analytic sphere weight function calculation" (FIG. 2A, left side), i.e., the BEM is used to transform the dipole source parameters into weight function values. Within the BEM or FEM, this transformation can be done either by the standard method [see for example, Fletcher D. J.: The Standard Boundary Element Method for Dipole Source Localization, Section 2.4 in *The Lead Field Analysis Algorithm for Dipole Source Localization*, University of California at Berkeley, 1994; or Fletcher D. J., et. al.: Improved Method for Computation of Potentials in a Realistic Head Shape Model, *IEEE Transactions on Biomedical Engineering*, 42(11):1094–1104, 1994] or by using the new Lead Field Analysis method of the present invention. In either case there is an initial calculation (A1 or B1 in FIG. 2B) which is computationally expensive, but only needs to be done once. This is followed by another calculation which is inexpensive and needs to be done repeatedly (A2 or B2 in FIG. 2B), as required by the iterations in the DSL computation (FIG. 2A).

If the brain-generator parameters are being estimated by means of a MUSIC method, then use of the Lead Field Analysis method is similar to that shown in FIG. 2. The differences are related to the MUSIC algorithm, which computes the optimal orientation of generators across a grid of locations within the non-spherical volume. The MUSIC computation requires a transformation from generator grid-location to weight function values, as part of the method. The algorithm used in the Lead Field Analysis provides weight function values for the grid points used by MUSIC, just as the Lead Field Analysis provides weight function values for different locations for DSL.

In determining nervous-system-generator parameters, different source characterizations may be used. These include distributed sources, multipole sources, dipoles with a finite distance between the poles (called finite dipoles), and dipoles in which both poles are at a single point (called point dipoles). Our Lead Field Analysis invention applies to any and all of these source characterizations.

SUMMARY

The invention is an improved machine and method for converting recordings of electric potentials into nervous-system-generator parameters that can be used by clinicians and researchers to evaluate generators of nervous system activity, whether it be in the central nervous system or peripheral nervous system. The machine and method utilize as inputs, physiological recordings made at sites remote from the generator, data on the shapes of boundaries, data on the locations of recording points, and the material properties of volumes within the region being analyzed. Within the machine and method is a computation which uses weight function values, such weight function values corresponding to the electric potentials which would be generated across the electrodes by a generator with unit magnitude. To determine these weight function values, the invention teaches the use of Lead Field Analysis in a boundary-element or finite-element method to compute the electric potentials and/or electric fields at the generator locations, due to current applied at the electrode locations. These electric potentials and/or electric fields can then be used to compute the weight function values, which in turn are used by the machine and method using a B-GSC computation to estimate and display the nervous-system-generator parameters of interest to the clinicians or researchers.

In one form, the invention is a machine comprising a computer for converting electrical recordings of the nervous system into displayed nervous-system-generator parameters, the machine comprising:

a. means for receiving and storing data comprised of electrical recordings at one or more time points from one or more recording channels, b. means for receiving and storing model data comprised of:
  1. locations and order of the mesh points defining each element,
  2. locations and order of the nodes on each element,
  3. shape functions defining the surface across each element,
  4. basis functions providing an approximation of the electric potential and electric flux density solutions across each element,
  5. material property data,
  6. locations of the recording electrodes in the model;

c. means for computing, using a boundary-element method, the electric potentials on nodes of all boundaries, or the electric potentials and electric flux densities on nodes on at least 1 boundary ($b_1$) encompassing the volume of interest and electric potentials on nodes on all boundaries ($b_2 \ldots b_n$) within $b_1$ describing junctions between volumes with different material properties that would occur due to a current of specified magnitude at the location of at least one recording electrode.

d. means for determining the weight function values for a specified generator at a specified location, from at least one of the electric potentials at the generator location or the electric fields at the generator location, said electric potentials or electric fields being derived from the results of the computation in subparagraph c, e. means for determining the electrical generator parameters, and f. means for displaying the electrical generator parameters determined according to subparagraph e.

In another form, the invention is a machine comprising a computer for converting electrical recordings of the nervous system into displayed nervous-system-generator parameters, the machine comprising:

a. means for receiving and storing data comprised of electrical recordings at one or more time points from one or more recording channels, b. means for receiving and storing model data comprised of:
  1. locations and order of the mesh points defining each element,
  2. locations and order of the nodes on each element,
  3. shape functions defining the volume of each element,
  4. basis functions providing an approximation of the electric potential and electric flux density solutions across each element,
  5. material property data,
  6. locations of the recording electrodes in the model;

c. means for computing, using a finite-element method, the electric potentials on nodes of the elements containing the electrical generators that would occur due to a current of specified magnitude at the location of at least one recording electrode.

d. means for determining the weight function values for a specified generator at a specified location from at least one of the electric potentials at the generator location or the electric fields at the generator location, said electric potentials or electric fields being derived from the results of the computation in subparagraph c, e. means for determining the electrical generator parameters, and f. means for displaying the electrical generator parameters determined according to subparagraph e.

In yet another form, the invention is a method for converting electrical recordings of the nervous system into displayed nervous-system-generator parameters, the method comprising:

a. programming a general purpose computer to receive and store data comprised of electrical recordings at one or more time points from one or more recording channels, b. programming a general purpose computer to receive and store model data comprised of:
  1. locations and order of the mesh points defining each element,
  2. locations and order of the nodes on each element,
  3. shape functions defining the surface across each element,
  4. basis functions providing an approximation of the electric potential and electric flux density solutions across each element,
  5. material property data,
  6. locations of the recording electrodes in the model;

c. programming the computer to compute, using a boundary-element method, the electric potentials on nodes of all boundaries, or the electric potentials and electric flux densities on nodes on at least 1 boundary ($b_1$) encompassing the volume of interest and electric potentials on all boundaries ($b_2 \ldots b_n$) within $b_1$ describing junctions between volumes with different material properties that would occur due to a current of specified magnitude at the location of at least one recording electrode.

d. programming the computer to compute the weight function values for a specified generator at a specified location, from at least one of the electric potentials at the generator location or the electric fields at the generator location, the electric potentials or electric fields being derived from the results of the computation in subparagraph c, e. programming the computer to compute the electrical generator parameters, and f. displaying the electrical generator parameters determined according to subparagraph e.

In yet another form, the invention is a method for converting electrical recordings of the nervous system into displayed nervous-system-generator parameters, the method comprising:

a. programming a general purpose computer to receive and store data comprised of electrical recordings at one or more time points from one or more recording channels, b. programming a general purpose computer to receive and store model data comprised of:
  1. locations and order of the mesh points defining each element,
  2. locations and order of the nodes on each element,
  3. shape functions defining the volume of each element,
  4. basis functions providing an approximation of the electric potential and electric flux density solutions across each element,
  5. material property data,
  6. locations of the recording electrodes in the model;

c. programming the computer to compute, using a finite-element method, the electric potentials on nodes of the elements containing the electric generators that would occur due to a current of specified magnitude at the location of at least one recording electrode.

d. programming the computer to determine the weight function values for a specified generator at a specified location from at least one of the electric potentials at the generator location or the electric fields at the generator location, the electric potentials or electric fields being derived from the results of the computation in subparagraph c, e. programming the computer to determine the electrical generator parameters, and f. displaying the electrical generator parameters determined according to subparagraph e.

BRIEF DESCRIPTION OF THE DRAWINGS

These and other features, aspects, and advantages of the present invention will become better understood with regard to the accompanying drawings where:

FIG. 3 (A and B) is a diagram showing one embodiment of the invention, where the weight function values provided by the invention are used in an iterative process to determine the nervous-system-generator parameters from recorded potentials.

COPYRIGHT

Source code useful for making and using the present invention is protected by copyright. The copyrighted code includes the "Lead Field Computer Program" code covered by US Copyright Registration TXu 676-947, registered Mar. 1, 1995; "Lead Field Computer Program II" code and "DSL Computer Program" code, both of which were sent to the US Copyright Office on Jun. 27, 1996 for registration. The code is available for review at the United States Copyright Office.

SYSTEM CONTEXT OF THE INVENTION

This invention is executable, for example, on a general purpose computer such as an International Business Machines computer IBM RS/6000, model 530, with 64 MB random access memory, and 2.3 GB hard disk space, running the operating system IBM AIX Version 3 for the RISC System/6000, using source code compiled by the AIX XL Fortran compiler and the AIX XL C compiler. The hardware is described in Publication SA23-2619, "IBM RISC System/6000 Technology", IBM Product Design and Development Advanced Workstations Division, IBM Corp., 1990. The operating system is described in "AIX General Concepts and Procedures for RISC System/6000", IBM Corp., Fourth Edition, 1992. The Fortran compiler is described in Publication SC09-1354-01, "AIX XL Fortran Compiler/6000 User's Guide Version 2.2.", IBM Corp., 1991. The C compiler is described in "XL C Reference Manual", IBM Corp., Fourth Edition, 1992.

DEFINITIONS

In the present specification and claims, reference will be made to phrases and terms of art that are expressly defined for use herein, including use in the claims, as follows:

Electrical Generator Parameters: The values necessary to characterize a mathematical model of an electrical source. For example, a current point dipole source can be characterized by a location in space, an orientation, and a magnitude.

Mesh: The nodes, mesh points and connectivity information which, taken with the associated basis functions and shape functions, define the discrete domains over which the boundary-element or finite-element problem is to be solved.

Model: The mesh defining the domain to be analyzed by the finite-element or boundary-element method, along with the associated material properties, recording electrode locations, boundary conditions and source configuration.

Mesh Points: Discrete locations in space used with the shape functions to define the geometry of the model. For the boundary-element method, these are locations on a set of surfaces defining the problem. For the finite-element method, these are locations throughout the volume.

Nodes: Discrete locations in space used with the basis functions to represent the potential and/or flux density solutions. For a given set of boundary conditions and/or source configurations, potentials and/or flux densities are calculated at each of the nodes in the model. Potentials and/or flux densities at any location in the model can be obtained using the values of the potential and/or flux density at the nodes and the basis functions.

Element: A discrete region of space with relatively simple geometry, within which the solution to the Poisson equation can be well approximated by some simple basis functions. This region of space is defined by a set of mesh points, their associated shape functions, and connectivity information. The Poisson equation is solved at a set of nodes located within the element and this solution can be interpolated to any arbitrary point within the element using the basis functions.

Shape Functions: Functions in one, two or three dimensional space which are used to define the location of any arbitrary point within an element by blending the locations of a finite set of mesh points.

Basis Functions: Functions in one, two, or three dimensional space which are used to define the potential or flux density at any arbitrary point within an element by blending the value of potential or flux density at a finite set of nodes.

Volume of Interest: Any sub-volume of the model containing the neural source of interest.

Fundamental Potential Solution: The potential which would be generated at a specific location in free space by a point current source at a specific location.

Fundamental Flux Solution: The electric flux density which would be generated at a specific location in an infinite homogeneous medium with unit conductivity by a point current source at a specific location.

Weight Function Value: The value of the potential difference between two locations (usually a pair of recording electrodes) generated by a unit-magnitude generator at a location of interest.

Material Property: At least one of the following: conductivity, impedance, directionally dependent conductivity, directionally dependent impedance.

Electric Potential: The work done by an external force to move a unit charge from one point to another.

Electric Flux Density: A measure of the amount of charge flowing through a given point in a given direction.

Electric Field: The force at a point exerted on a particle of unit charge.

Conductivity: The constant of proportionality defining the relationship between current density and electric field at a given point within a medium.

Current density: A measure of the strength and direction of the current flow at a given point in space.

Current source: A point or volume where the divergence of current density is non zero, and the sum of the divergence is positive. The sum is the strength or magnitude of the current source.

Current sink: A point or volume where the divergence of current density is non zero, and the sum of the divergence is negative. The sum is the strength or magnitude of the current source.

Current dipole: A combination of a current source and a current sink with equal magnitude. The product of the magnitude and the separation between the sink and the source, with the direction from the sink to the source, is called the moment of the current dipole.

Point dipole: A current dipole with finite moment and infinitesimal separation between the source and the sink.

DESCRIPTION

A machine in which the present invention can be made and used is diagrammed in FIG. 1. Steps for use of the invention with a source analysis program are shown in the flowchart of FIG. 3A, which shows in more detail the steps that occur in the named programs in FIG. 1. In FIG. 3A, the box labeled "Source Analysis Program" indicates one example of a computer program that transforms electric potentials recorded at the surface into nervous-system-generator parameters using an iterative procedure. When the machine is operated, an initial solution to the generator parameters is chosen, which, in turn determines a set of weight function values by means of the LFA, which is described below. Using the weight function values from the LFA, the source analysis program then does a linear fit for nervous-system-generator magnitude functions, from which predicted surface potentials are derived. These predicted surface potentials are then compared to the potentials recorded at the electrode locations, and the differences are compared, using any of a variety of error functions. Typically, the least-square error is computed. If that error is greater than a specified amount, then a new set of source parameters are chosen, and the process repeated, as indicated by the return arrow labeled "adjust parameters" in FIG. 3A. The new set of source parameters can be chosen by any of a variety of methods, including the Simplex method, a gradient descent method, or simulated annealing. When the error measure is within a given tolerance, the solution to the nervous-system-generator parameters is then displayed as graphs of magnitude functions over time, and graphically as locations and orientations within the volume of interest. The solutions can also be presented in other ways, including deviations from normal.

Figures 3, 3B:
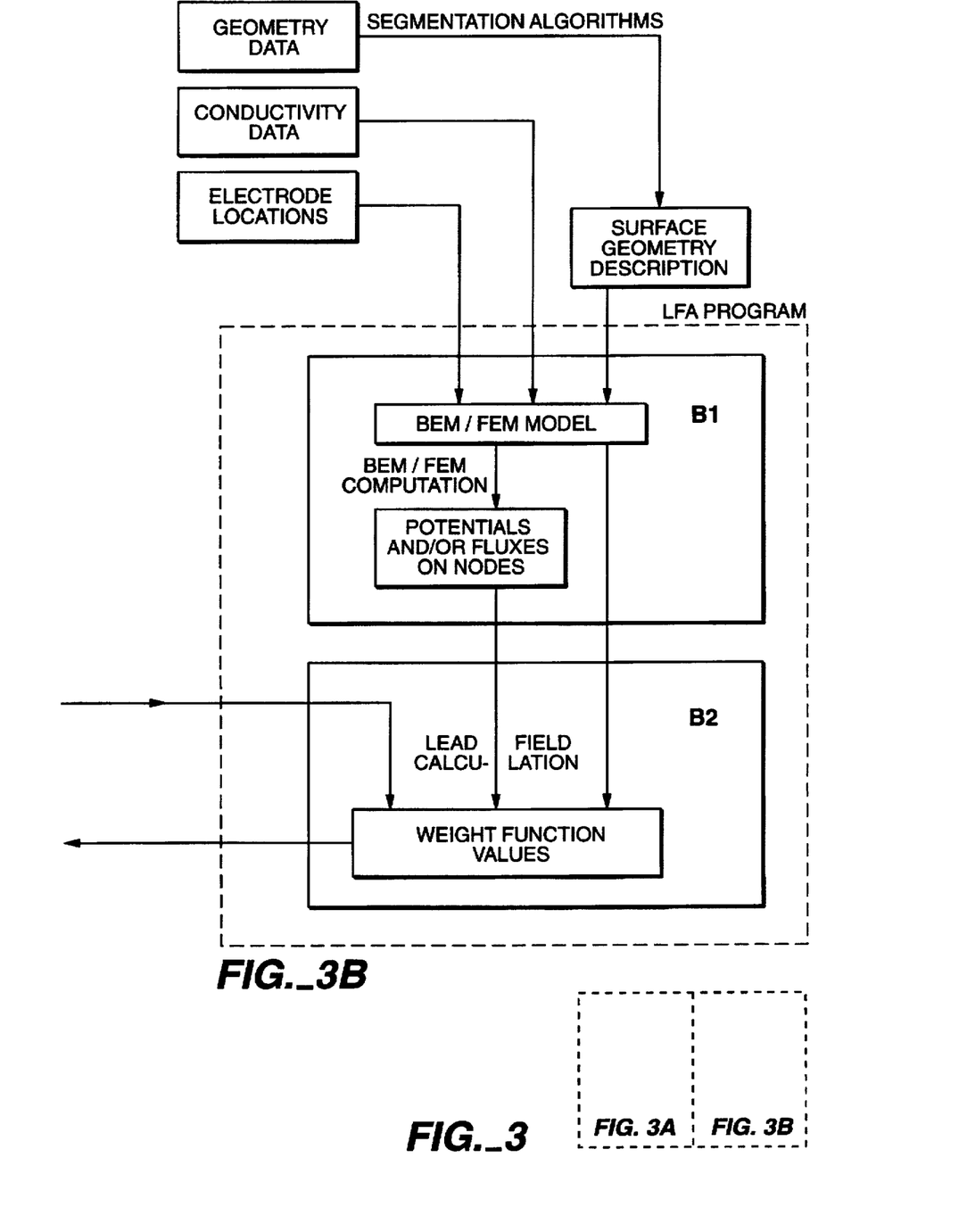
Figure 3A:
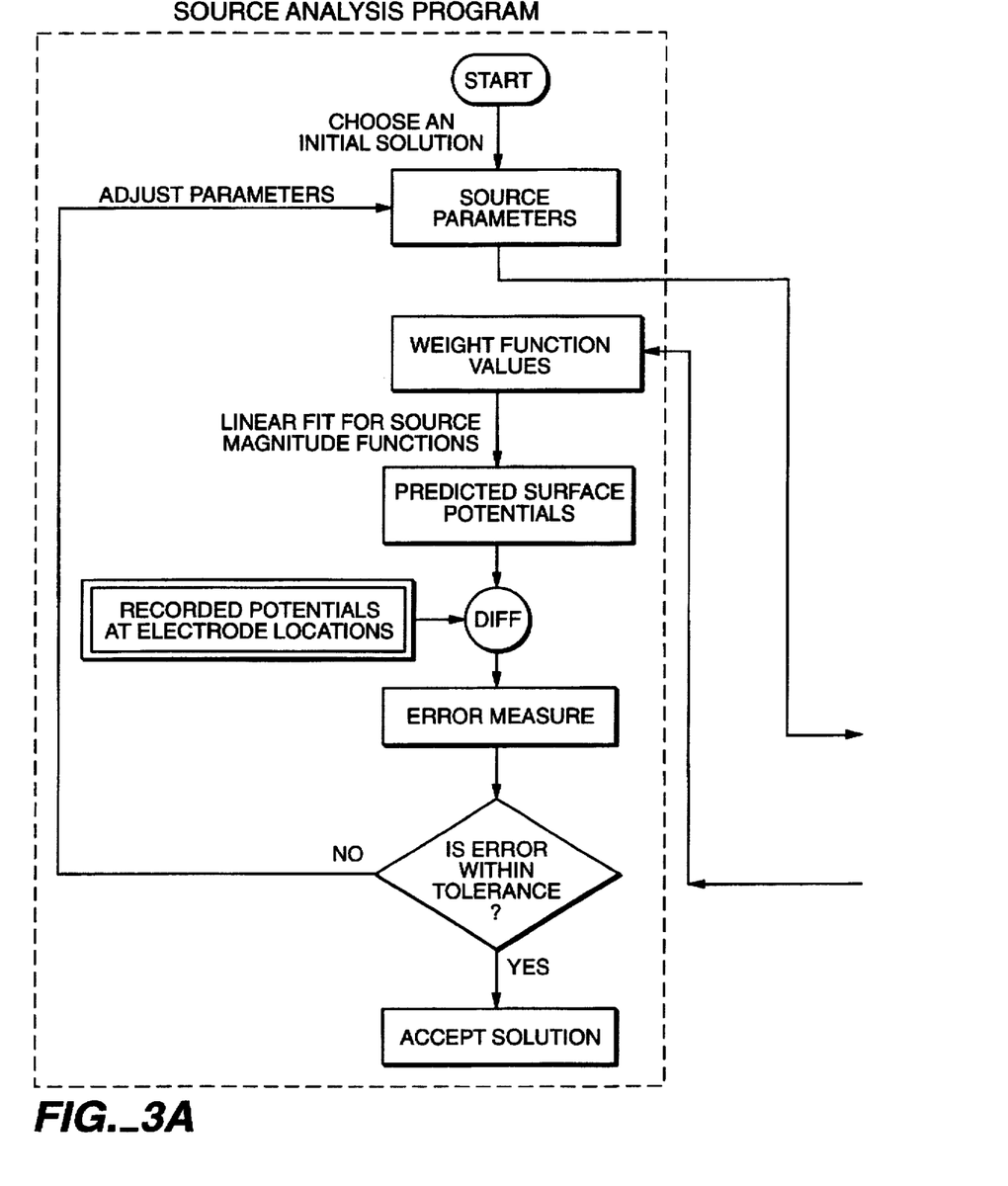

The LFA program shown in flowchart steps B1 and B2 in FIG. 3B provides the weight function values when it is provided with the following: 1) source parameters, 2) geometric data as to: a) the shape and locations of all boundaries or volumes, b) location of electrodes, and 3) material property data. In so doing, the LFA program uses either the Boundary-Element Method (BEM) or the Finite-Element Method (FEM). The BEM involves the solution of the Poisson's Equation within a domain using a discretization of the boundaries dividing each homogeneous compartment of the domain. The FEM solves this equation by discretizing each of the volumes comprising the domain. The Poisson's Equation for the potential V due to a current source distribution I(r) with a volume conductor is given by, $$\nabla \cdot (\sigma(r) \nabla V(r)) = -I(r) \qquad \text{(Eq. 1)}$$

where r is a location in the volume conductor, σ(r) is the conductivity at r, and all vector quantities are in a bold font. The result of the discretization of the Poisson equation is a set of linear equations that can be used to find the values of electric potentials and electric flux densities on the discretized borders or within the discretized volume, subject to the appropriate boundary conditions and source configuration. A derivation of the discretized equations for the BEM is given in Brebbia [*Boundary Elements: An Introductory Course, Computational Mechanics*, Southampton, 1989]; derivation of the discretized equations for the FEM is given in Lewis and Ward [*The Finite Element Method: Principles and Applications*. Addision-Wesley, 1991].

The invention uses the BEM or the FEM to compute the weight function values by means of the Reciprocity Theorem. The Reciprocity Theorem states that the potential difference $V_{ab}$ between two points a and b due to a point dipole at location r with moment D is equivalent to the dot product of 1) the electric field E at r due to a current $I_{ab}$ applied across the two points a and b, and 2) the dipole moment D, divided by the current $I_{ab}$ [Rush, Driscoll, *IEEE Trans Biomed Eng*, 16:1, 15–22, 1969]:

$$V_{ab} = \frac{E \cdot D}{I_{ab}} \qquad \text{(Eq. 2)}$$

E is also called the "lead field". In all the following formulas, where $I_{ab}$ appears, it denotes the current injected in the BEM or FEM computation of the lead fields or the potentials. The weight functions that are used by any of the B-GSC algorithms mentioned above, are computed as follows. By definition, the weight function ($W_{ab}(r)$), corresponding to an electrode pair ab and a point dipole at point r is defined as the voltage $V_{ab}$ due to a unit-magnitude current dipole at location r. Given the lead field E at the dipole location (due to injecting a unit-magnitude current between points a and b), and given the dipole moment D, the weight function is calculated from the equation, $$W_{ab}(r) = \frac{E \cdot D}{D I_{ab}} \qquad \text{(Eq. 3)}$$

where D is the magnitude of D.

Given a BEM mesh (the nodes, mesh points and connectivity information which, taken with the associated basis functions and shape functions, define the discrete domains over which the boundary-element problem is to be solved) or an FEM mesh (the nodes, mesh points and connectivity information which, taken with the associated basis functions and shape functions, define the discrete domains over which the finite-element problem is to be solved), the LFA calculates the weight functions by a two step process. The first step, called the Initialization Procedure (Box B1 in FIG. 2B and FIG. 3B), is accomplished by simulating current injection at one electrode of a pair of electrodes comprising a single recording channel and current extraction at the other electrode. A standard BEM or FEM computation is then performed which calculates the electric potential u and/or normal flux q at each of the nodes in the model due to the application of these boundary conditions. No other sources are simulated within the volume. This computation is repeated for each of the recording channels and a separate set of values for u and/or q are computed. Note that this portion of the computation depends only upon the geometry of the volume of interest, the material properties of each volume, and the locations of the electrodes, not upon any characteristics of the neural source being modeled.

The second step of the LFA computation, called the Weight Function Computation (Box B2 in FIG. 2B and FIG. 3B), requires the calculation of the electric potential and/or electric field at the point or points corresponding to the location(s) of the neural generator(s) needed for the B-GSC analysis. This calculation can be done in a number of ways, depending upon whether the BEM or FEM was used in the Initialization Procedure, and the types of elements used in the model. If the BEM is used, the electric potential or electric field at any point in the volume of interest can be estimated utilizing either the electric potentials at the nodes on all shells in the model (the All Shells (AS) method), or the electric potentials and electric flux densities on the shell or shells of the model which separate the volume of interest from the rest of the volume (the Single Shell (SS) method). The electric potential or electric field at the source location r can be obtained from the AS method utilizing Green's theorem as follows:

$$u(r) = \qquad \text{(Eq. 4)}$$

$$\sum_{i=1}^{N} \frac{\sigma_{i-1} - \sigma_i}{\sigma_k} \int_{S_i} u(r') \nabla_{r'} u^*(r,r') \cdot ds - \frac{1}{\sigma_k} \int_{S_1} u^*(r,r') j \cdot ds$$

$$E(r) = -\nabla_r u(r) \qquad \text{(Eq. 5)}$$

where N is the number of nested shells and here the I-th shell is entirely contained in the (I−1)th shell (when dealing with other boundaries, Equation 4 will have a different form). The $\sigma_i$ is the conductivity of the volume between the I-th and (I−1)th shells, $\sigma_0 \equiv 0$. Within the integral, r' is on the I-th surface, s. $u^*(r,r')$ is the fundamental potential solution. j is the specified current density on the outermost surface. $\sigma_k$ is the conductivity of the volume containing the location r. $\nabla_r$ means the derivative is taken with respect to the variable r; the same is true for $\nabla_{r'}$. In the numerical calculation, the shells are discretized into small elements. On each element, the integration is carried out utilizing the shape functions and the basis functions.

Alternatively, the electric potential and electric field at the source location r can be computed with the SS method utilizing Green's Theorem as follows:

$$u(r) = \int_s u^*(r,r') \nabla_{r'} u(r') \cdot ds - \int_s u(r') \nabla_{r'} u^*(r,r') \cdot ds \qquad \text{(Eq. 6)}$$

$$E(r) = -\nabla_r u(r) \qquad \text{(Eq. 7)}$$

where s is the surface separating the homogeneous volume containing point r from the rest of the volume.

If the FEM is used, the electric field and/or electric potential at any point in the brain region can be estimated by interpolating the electric potentials at the nodes on the volume element containing the location of interest using the basis functions (for the electric potential) or the derivatives of the basis functions in three orthogonal directions (for the electric field).

Once the electric potential or electric field at the source location is known, the weight function, i.e. the electric potential across the electrode pair due to a unit-magnitude generator at that location can be computed. There are at least three basic types of generators for which the weight functions can be obtained using this method. Each is described separately below.

Point Dipole Sources

For the case of a point dipole, the electric field at the dipole location can be used to calculate the weight function values utilizing Equation 3 above.

Distributed Sources

In the distributed source case, a current distribution is specified at each stage of the DSL or MUSIC computation. In FIG. 3A this is indicated by the box labeled "source parameters". This definition consists of a specified current distribution as a function of location ρ(r). The magnitude of the distributed source current is $I_{dis}$. Thus, the current density at each point on the source is given by $I_{dis}\rho(r)$. We now describe the method of computing the electric potentials across a set of electrodes due to a defined distributed source. The distributed source has a fixed known distribution ρ(r) except for the magnitude of the current $I_{dis}$ which is determined by the DSL computation. There is only one weight function involved, denoted by $W_{ab}^{dis}$. The electric potential $V_{ab}$ needed in the DSL computation is computed by $V_{ab}=I_{dis}W_{ab}^{dis}$. The distributed source weight function $W_{ab}^{dis}$ is computed (by discretization) over the source volume V as follows, $$W_{ab}^{dis}(r) = \frac{1}{I_{ab}} \int_V u(r'-r)\rho(r'-r)d\tau' \qquad \text{(Eq. 8)}$$

where u(r) is the electric potential at location r due to a current $I_{ab}$ injected across the electrodes ab and dτ' is an infinitesimal volume element at r'. u(r) is computed as described above using either the FEM, the BEM AS or the BEM IS method. At each step of the iteration, DSL specifies r, which is used in Equation 8.

Finite Dipole Source

In the case of a finite dipole the weight function $W_{ab}^f$ is computed from the following equation:

$$W_{ab}^f = \frac{u(r_+) - u(r_-)}{l_{ab}} \qquad \text{(Eq. 9)}$$

where $u(r_+)$ is the electric potential at the source and $u(r_-)$ is the electric potential at the sink of the finite dipole due to the injected current $I_{ab}$. Using the weight function in Equation 9, the potential due to a finite dipole is calculated from $V_{ab}=I_f W_{ab}^f$ where $I_f$ is the current of the finite dipole. At each step of the iteration, the source analysis program specifies $r_+$ and $r_-$ which are used in Equation 9.

The electric potential u at the source and sink locations needed in Equation 9 is calculated as described above using either the BEM AS, BEM IS or FEM.

In carrying out the numerical integrations and solving the matrix equations of the present invention, techniques known to improve the accuracy in the standard BEM and FEM can also be applied.

Although the LFA computation was described to be done for each recording channel, by means of algebraic manipulation well within the skill of one skilled in this art, it is easy to show that the weight function can be obtained with other current injection patterns on the recording electrode sites. For example, if the desired currents are plus (injection) at electrode A, and minus (extraction) at electrode B, then this could be obtained from data obtained by pairing electrode A with point C, and pairing electrode B with point C, as in the following equation:

$$A-B=(A-C)-(B-C) \qquad \text{(Eq. 10)}$$

The source code used to create one version of the invention in a specified general purpose computer, whose purpose is to compute locations of brain generators in a head shape, is available for review at the United States Copyright Office. The copyright in the source code was registered Mar. 1, 1995 as TXu 676-947. An example of the operation of a version of this invention is shown in Fletcher D. J.: *The Lead Field Analysis Algorithm for Dipole Source Localization*, University of California at Berkeley, 1994 Ph.D., in which the source code was used to study the accuracy of lead fields when used with eccentric dipole sources. Additional source code that can be used to make and use the present invention has been submitted to the United States Copyright Office for registration. See the heading, COPYRIGHT, above.

While the invention has been illustrated with respect to specific hardware and software, it should be understood that alternative general or specific purpose computing equipment, and other software, or hard-wired logic circuitry could be used in practicing the invention. In addition, although the present invention has been described in considerable detail with reference to certain preferred versions thereof, other versions are possible. Therefore, the spirit and scope of the appended claims should not be limited to the description of the preferred versions contained herein.

We claim:

1. A machine comprising a computer for converting electrical recordings of the nervous system into displayed nervous-system-generator parameters using a computational model, said model defined by parameters including mesh points, nodes, elements, shape functions defining the surface across each element, basis functions providing an approximation of electric potential and electric flux density solutions across each element, volumes of interest, electrical generator parameters, and electrical material property data across the volumes of interest, the machine comprising:

a. means for receiving and storing data comprised of electrical recordings at one or more time points from one or more recording channels, said means including at least one recording electrode, b. means for receiving and storing model data comprised of:
      1. locations and order of the mesh points defining each element,
      2. locations and order of the nodes on each element,
      3. shape functions defining the surface across each element,
      4. basis functions providing an approximation of the electric potential and electric flux density solutions across each element,
      5. electrical material property data across the volumes of interest,
      6. locations of said at least one recording electrode in the model;
      7. initial electrical generator parameters, including initial generator-location;

c. means for computing, using a boundary element method, the electric potentials on nodes of all boundaries, or the electric potentials and electric flux densities on nodes on at least 1 boundary ($b_1$) encompassing the volumes of interest and electric potentials on nodes on all boundaries ($b_2 \ldots b_n$) within $b_1$ describing junctions between volumes with different material properties that would occur due to a current of specified magnitude at the location of said at least one recording electrode, d. means for determining weight function values for said initial generator parameters, from at least one of the electric potentials at said initial generator location or the electric fields at said initial generator location, said electric potentials or electric fields being derived from said electric potentials and/or flux densities computed in subparagraph c, e. means for determining the electrical generator parameters, and f. means for displaying said electrical generator parameters determined according to subparagraph e and/or said weight function values according to subparagraph d.

2. A machine according to claim 1 wherein the means for determining the electrical generator parameters of step 1e comprises at least one of: (1) means for iteratively calculating a solution to the electrical generator parameters, said means varying at least one of said electrical generator parameters, and recomputing weight function values as derived in subparagraph 1 d based on said varied electrical generator parameters, or (2) means for calculating a solution that utilizes a set of pre-computed weight function values, as derived in subparagraph 1 d, across a grid of location-points within the volumes of interest.

3. A machine comprising a computer for converting electrical recordings of the nervous system into displayed nervous-system-generator parameters using a computational model, said model defined by parameters including mesh points, nodes, elements, shape functions defining the surface across each element, basis functions providing an approximation of electric potential and electric flux density solutions across each element, volumes of interest, electrical generator parameters, and electrical material property data across the volumes of interest, the machine comprising:

a. means for receiving and storing data comprised of electrical recordings at one or more time points from one or more recording channels, said means including at least one recording electrode,
  b. means for receiving and storing model data comprised of:
    1. locations and order of the mesh points defining each element,
    2. locations and order of the nodes on each element,
    3. shape functions defining the surface across each element,
    4. basis functions providing an approximation of the electric potential and electric flux density solutions across each element,
    5. electrical material property data across the volumes of interest,
    6. locations of said at least one recording electrode in the model;
    7. initial electrical generator parameters, including initial generator-location;
  c. means for computing, using a finite element method, the electric potentials on nodes of the elements containing the electric generators that would occur due to a current of specified magnitude at the location of said at least one recording electrode,
  d. means for determining weight function values for said initial generator parameters, from at least one of the electric potentials at said initial generator location or the electric fields at said initial generator location, said electric potentials or electric fields being derived from said electric potentials and/or flux densities computed in subparagraph c,
  e. means for determining the electrical generator parameters, and
  f. means for displaying said electrical generator parameters determined according to subparagraph e and/or said weight function values according to subparagraph d.

4. A machine according to claim 3 wherein the means for determining the electrical generator parameters of step 3e comprises at least one of: (1) means for iteratively calculating a solution to the electrical generator parameters, said means varying at least one of said electrical generator parameters, and recomputing weight function values as derived in subparagraph 3 d based on said varied electrical generator parameters, or (2) means for calculating a solution that utilizes a set of pre-computed weight function values, as derived in subparagraph 3 d, across a grid of location-points within the volumes of interest.

5. A method for converting electrical recordings of the nervous system into displayed nervous-system-generator parameters using a computational model, said model defined by parameters including mesh points, nodes, elements, shape functions defining the surface across each element, basis functions providing an approximation of electric potential and electric flux density solutions across each element, volumes of interest, electrical generator parameters, and electrical material property data across the volumes of interest, the method comprising:

a. programming a general purpose computer to receive and store data comprised of electrical recordings at one or more time points from one or more recording channels from at least one recording electrode,
  b. programming a general purpose computer to receive and store model data comprised of:
    1. locations and order of the mesh points defining each element,
    2. locations and order of the nodes on each element,
    3. shape functions defining the surface across each element,
    4. basis functions providing an approximation of the electric potential and electric flux density solutions across each element,
    5. electrical material property data across the volumes of interest,
    6. locations of said at least one recording electrode in the model;
    7. initial electrical generator parameters, including initial generator-location;
  c. programming the computer to compute, using a boundary element method, the electric potentials on nodes of all boundaries, or the electric potentials and electric flux densities on nodes on at least 1 boundary ($b_1$) encompassing the volumes of interest and electric potentials on nodes on all boundaries ($b_2 \ldots b_n$) within $b_1$ describing junctions between volumes with different material properties that would occur due to a current of specified magnitude at the location of said at least one recording electrode,
  d. programming the computer to compute the weight function values for said initial generator parameters, from at least one of the electric potentials at said initial generator location or the electric fields at said initial generator location, said electric potentials or electric fields being derived from said electric potentials and/or flux densities computed in subparagraph c,
  e. programming the computer to compute the electrical generator parameters, and
  f. displaying said electrical generator parameters determined according to subparagraph e and/or said weight function values according to subparagraph d.

6. A method according to claim 5 wherein the step of determining the electrical generator parameters of step 5e comprises at least one of: (1) iteratively calculating a solution to the electrical generator parameters, said step varying at least one of said electrical generator parameters, and recomputing weight function values as derived in subparagraph 5 d based on said varied electrical generator parameters, or (2) calculating a solution that utilizes a set of pre-computed weight function values, as derived of subparagraph 5 d, across a grid of location-points within the volumes of interest.

7. A method for converting electrical recordings of the nervous system into displayed nervous-system-generator parameters using a computational model, said model defined by parameters including mesh points, nodes, elements, shape functions defining the surface across each element basis functions providing an approximation of electric potential and electric flux density solutions across each element, volumes of interest, electrical generator parameters, and electrical material property data across the volumes of interest, the method comprising:

a. programming a general purpose computer to receive and store data comprised of electrical recordings at one or more time points from one or more recording channels from at least one recording electrode, b. programming a general purpose computer to receive and store model data comprised of:
 1. locations and order of the mesh points defining each element,
 2. locations and order of the nodes on each element,
 3. shape functions defining the surface across each element,
 4. basis functions providing an approximation of the electric potential and electric flux density solutions across each element,
 5. electrical material property data across the volumes of interest,
 6. locations of said at least one recording electrode in the model;
 7. initial electrical generator parameters, including initial generator-location;

c. programming the computer to compute, using a finite element method, the electric potentials on nodes of the elements containing the electric generators that would occur due to a current of specified magnitude at the location of said at least one recording electrode, d. programming the computer to determine the weight function values for said initial generator parameters, from at least one of the electric potentials at said initial generator location or the electric fields at said initial generator location, said electric potentials or electric fields being derived from said electric potentials and/or flux densities computed in subparagraph c, e. programming the computer to determine the electrical generator parameters, and f. displaying said electrical generator parameters determined according to subparagraph e end/or said weight function values according to subparagraph d.

8. A method according to claim 7 wherein the step of determining the electrical generator parameters of step 1e comprises at least one of: (1) iteratively calculating a solution to the electrical generator parameters, said step varying at least one of said electrical generator parameters, and recomputing weight function values as derived in subparagraph 7 d based on said varied electrical generator parameters, or (2) calculating a solution that utilizes a set of pre-computed weight function values, as derived of subparagraph 7 d, across a grid of location-points within the volumes of interest.

* * * * *